(12) United States Patent
Ishida et al.

(10) Patent No.: US 8,705,021 B2
(45) Date of Patent: Apr. 22, 2014

(54) INSPECTING DEVICE, INSPECTING METHOD, AND METHOD FOR MANUFACTURING OPTICAL FIBER

(75) Inventors: Itaru Ishida, Sakura (JP); Hiroki Hamaguchi, Sakura (JP)

(73) Assignee: Fujikura Ltd., Tokyo (JP)

( * ) Notice: Subject to any disclaimer, the term of this patent is extended or adjusted under 35 U.S.C. 154(b) by 30 days.

(21) Appl. No.: 13/527,111

(22) Filed: Jun. 19, 2012

(65) Prior Publication Data
US 2013/0027689 A1 Jan. 31, 2013

(30) Foreign Application Priority Data
Jul. 26, 2011 (JP) ................ 2011-163473

(51) Int. Cl.
*G01N 21/00* (2006.01)
(52) U.S. Cl.
USPC ........................... 356/73.1; 356/901
(58) Field of Classification Search
USPC ............ 356/73.1, 901; 385/123–127, 28; 65/377, 378, 393; 398/148
See application file for complete search history.

(56) References Cited

U.S. PATENT DOCUMENTS

| | | |
|---|---|---|
| 6,526,209 B1 | 2/2003 | Hasegawa et al. |
| 6,636,677 B2 | 10/2003 | Hasegawa et al. |
| 6,766,088 B2 | 7/2004 | Hasegawa et al. |
| 7,484,387 B2 | 2/2009 | Hasegawa et al. |
| 2001/0028775 A1 | 10/2001 | Hasegawa et al. |
| 2001/0038740 A1 | 11/2001 | Hasegawa et al. |
| 2002/0118938 A1 | 8/2002 | Hasegawa et al. |
| 2004/0170437 A1 | 9/2004 | Hasegawa et al. |
| 2011/0132037 A1 | 6/2011 | Ishida et al. |

FOREIGN PATENT DOCUMENTS

| | | |
|---|---|---|
| JP | 11132906 A | 5/1999 |
| JP | 2000171349 A | 6/2000 |
| JP | 2002-145634 A | 5/2002 |
| JP | 2002-249335 A | 9/2002 |
| JP | 2002-293562 A | 10/2002 |
| JP | 2006-160528 A | 6/2006 |
| WO | 2010116762 A1 | 10/2010 |
| WO | 2011/052541 A1 | 5/2011 |

OTHER PUBLICATIONS

Japanese Office Action Application No. 2011-163473; Sep. 3, 2013 with translation.

*Primary Examiner* — Tri T Ton
(74) *Attorney, Agent, or Firm* — Sughrue Mion, PLLC

(57) ABSTRACT

A detector sequentially detects intensity distribution of transmitted light which is transmitted through a center portion of a preform. A determining section determines at least one of a position of a through hole and a size thereof on the basis of a time series of a feature value in the intensity distribution.

12 Claims, 11 Drawing Sheets

FIG. 3
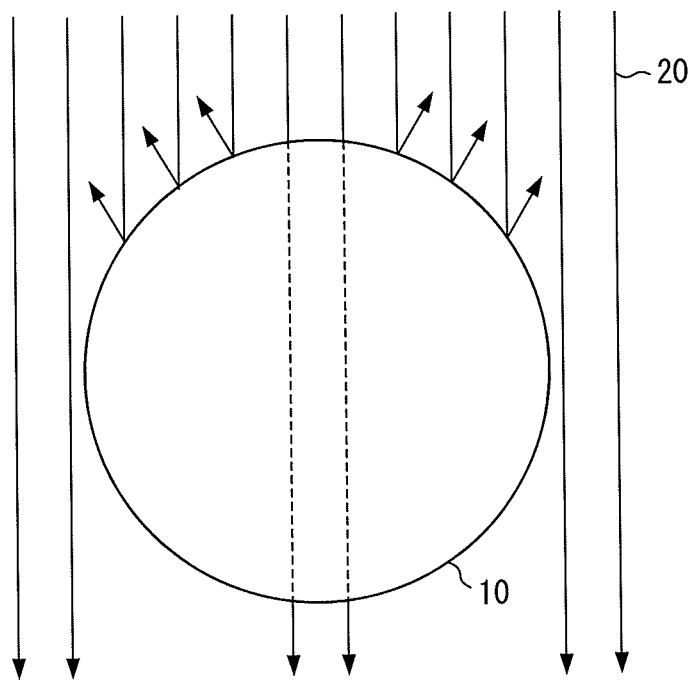
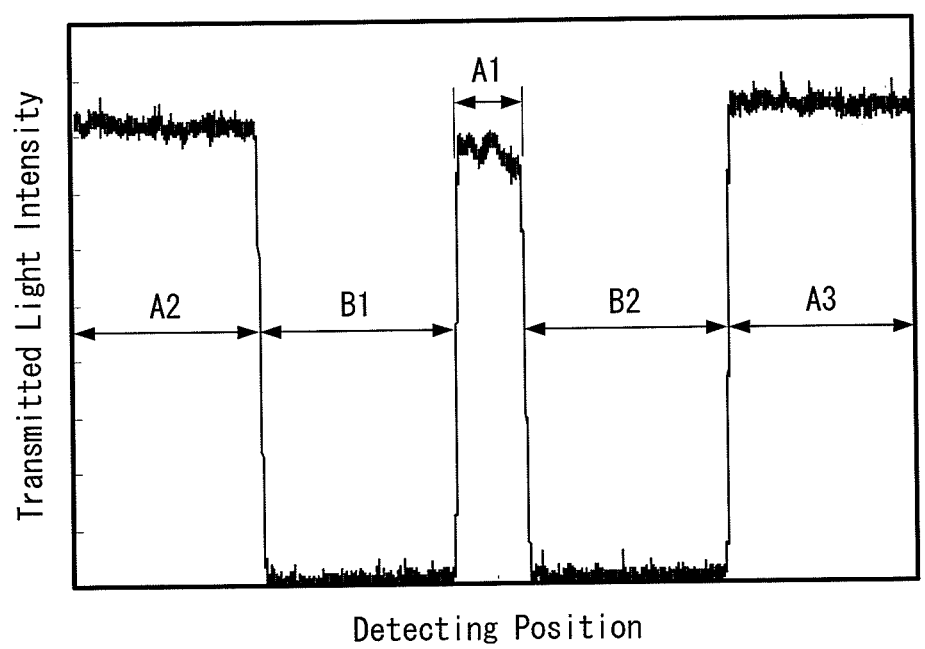

FIG. 4
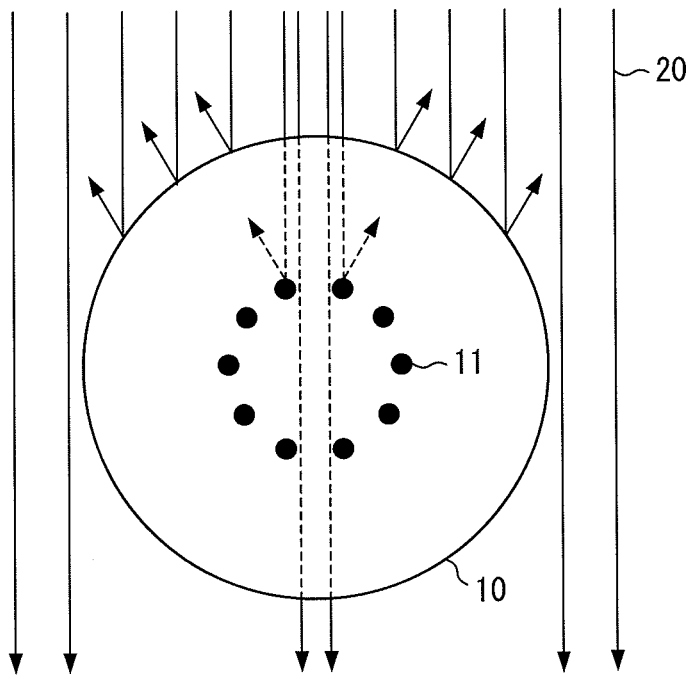
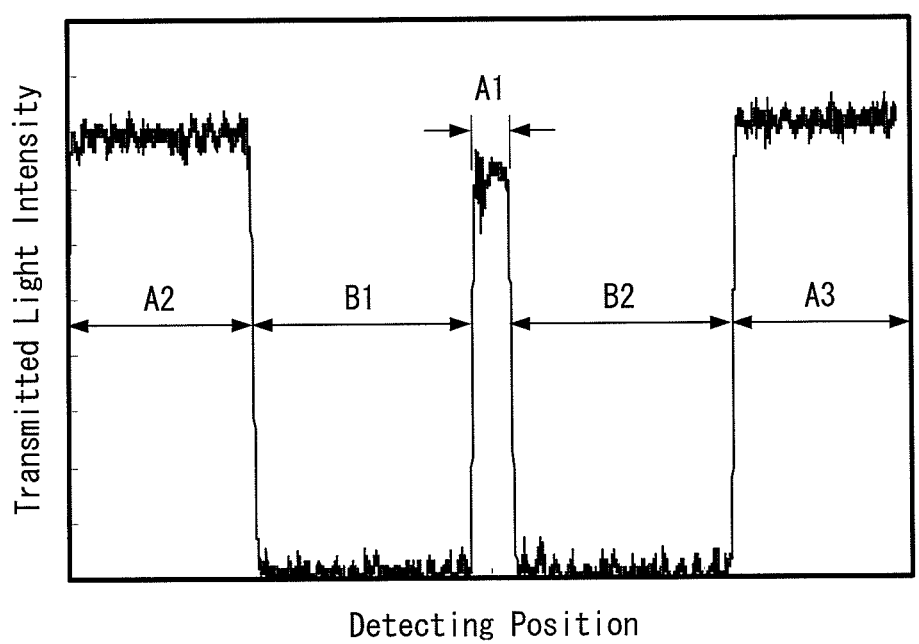

FIG. 5
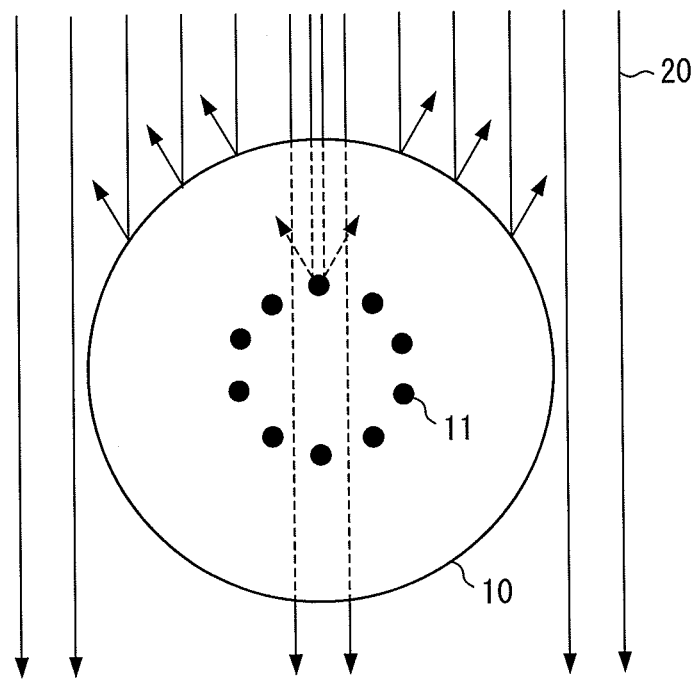
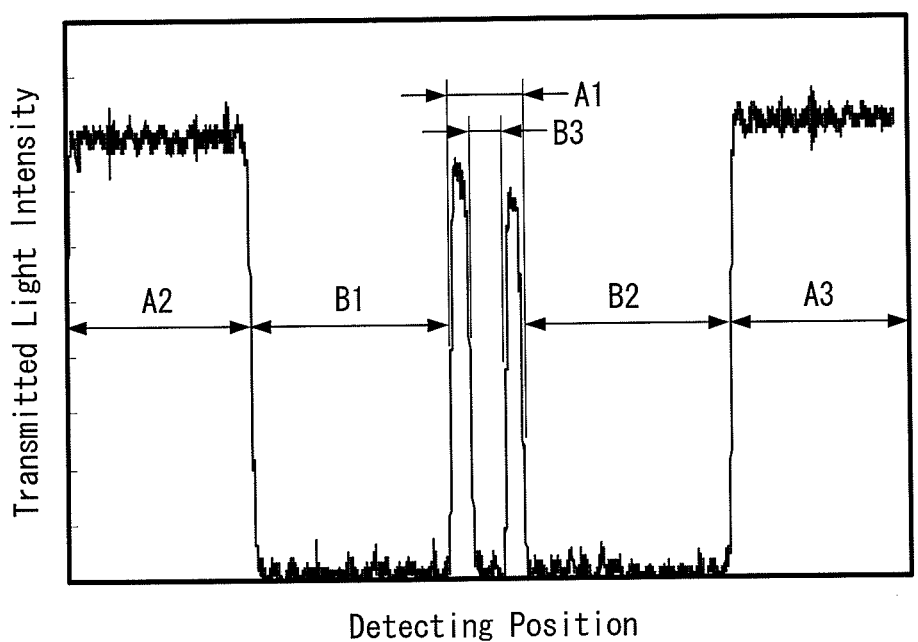

FIG. 8

| Measuring Position (mm) | | 10 | 200 | 400 | 600 | 800 |
|---|---|---|---|---|---|---|
| Interval Between Adjacent Through Holes (mm) | Through Hole #1 | 8.26 | 8.26 | 8.26 | 8.32 | 8.38 |
| | Through Hole #2 | 8.26 | 8.26 | 8.33 | 8.41 | 8.50 |
| | Through Hole #3 | 8.26 | 8.23 | 8.26 | 8.27 | 8.27 |
| | Through Hole #4 | 8.23 | 8.26 | 8.29 | 8.34 | 8.37 |
| | Through Hole #5 | 8.24 | 8.26 | 8.29 | 8.39 | 8.44 |
| | Through Hole #6 | 8.26 | 8.26 | 8.31 | 8.34 | 8.43 |
| | Through Hole #7 | 8.26 | 8.27 | 8.33 | 8.39 | 8.53 |
| | Through Hole #8 | 8.26 | 8.27 | 8.25 | 8.32 | 8.31 |
| | Average | 8.25 | 8.26 | 8.29 | 8.35 | 8.41 |
| | Maximum | 8.26 | 8.27 | 8.33 | 8.41 | 8.53 |
| | Minimum | 8.23 | 8.23 | 8.25 | 8.27 | 8.27 |

FIG. 9

| Measuring Position (mm) | | 10 | 200 | 400 | 600 | 800 |
|---|---|---|---|---|---|---|
| Interval Between Adjacent Through Holes (mm) | Through Hole #1 | 8.24 | 8.25 | 8.27 | 8.30 | 8.36 |
| | Through Hole #2 | 8.25 | 8.28 | 8.35 | 8.43 | 8.52 |
| | Through Hole #3 | 8.25 | 8.24 | 8.24 | 8.26 | 8.30 |
| | Through Hole #4 | 8.25 | 8.25 | 8.27 | 8.32 | 8.39 |
| | Through Hole #5 | 8.25 | 8.26 | 8.31 | 8.38 | 8.46 |
| | Through Hole #6 | 8.25 | 8.26 | 8.30 | 8.36 | 8.43 |
| | Through Hole #7 | 8.24 | 8.27 | 8.33 | 8.41 | 8.51 |
| | Through Hole #8 | 8.24 | 8.25 | 8.27 | 8.30 | 8.32 |
| | Average | 8.25 | 8.26 | 8.29 | 8.33 | 8.39 |
| | Maximum | 8.26 | 8.28 | 8.35 | 8.43 | 8.52 |
| | Minimum | 8.24 | 8.24 | 8.23 | 8.22 | 8.21 |

FIG. 11

| Measuring Position (mm) | | 10 | 200 | 400 | 600 | 800 |
|---|---|---|---|---|---|---|
| Width Of Through Holes (mm) | Through Hole #1 | 3.06 | 3.06 | 3.06 | 3.02 | 3.05 |
| | Through Hole #2 | 3.07 | 3.06 | 3.06 | 3.05 | 3.04 |
| | Through Hole #3 | 3.09 | 3.07 | 3.06 | 3.05 | 3.05 |
| | Through Hole #4 | 3.08 | 3.06 | 3.05 | 3.06 | 3.04 |
| | Through Hole #5 | 3.05 | 3.07 | 3.03 | 3.05 | 3.09 |
| | Through Hole #6 | 3.04 | 3.06 | 3.06 | 3.06 | 3.05 |
| | Through Hole #7 | 3.05 | 3.05 | 3.06 | 3.06 | 3.05 |
| | Through Hole #8 | 3.09 | 3.06 | 3.06 | 3.03 | 3.06 |
| | Average | 3.06 | 3.06 | 3.05 | 3.05 | 3.05 |
| | Maximum | 3.09 | 3.07 | 3.06 | 3.06 | 3.09 |
| | Minimum | 3.04 | 3.05 | 3.03 | 3.02 | 3.04 |

FIG. 12

| Measuring Position (mm) | | 10 | 200 | 400 | 600 | 800 |
|---|---|---|---|---|---|---|
| Width Of Through Holes (mm) | Through Hole #1 | 3.06 | 3.04 | 3.04 | 3.04 | 3.05 |
| | Through Hole #2 | 3.07 | 3.04 | 3.04 | 3.04 | 3.05 |
| | Through Hole #3 | 3.08 | 3.06 | 3.06 | 3.06 | 3.06 |
| | Through Hole #4 | 3.06 | 3.04 | 3.04 | 3.04 | 3.03 |
| | Through Hole #5 | 3.07 | 3.05 | 3.05 | 3.04 | 3.07 |
| | Through Hole #6 | 3.06 | 3.04 | 3.04 | 3.04 | 3.04 |
| | Through Hole #7 | 3.06 | 3.04 | 3.04 | 3.04 | 3.03 |
| | Through Hole #8 | 3.06 | 3.04 | 3.04 | 3.04 | 3.04 |
| | Average | 3.06 | 3.04 | 3.04 | 3.04 | 3.05 |
| | Maximum | 3.08 | 3.06 | 3.06 | 3.06 | 3.07 |
| | Minimum | 3.06 | 3.04 | 3.04 | 3.04 | 3.03 |

INSPECTING DEVICE, INSPECTING METHOD, AND METHOD FOR MANUFACTURING OPTICAL FIBER

This Nonprovisional application claims priority under 35 U.S.C. §119 on Patent Application No. 2011-163473 filed in Japan on Jul. 26, 2011, the entire contents of which are hereby incorporated by reference.

TECHNICAL FIELD

The present invention relates to (i) an inspecting device for a preform which is a base material of an optical fiber in which a hole is formed, that is, in which through holes are formed and (ii) an inspecting method of the preform. Further, the present invention relates to a method for manufacturing the optical fiber.

BACKGROUND ART

In recent years, a holey fiber becomes popular as an optical fiber suitable for a long transmission distance. The holey fiber is an optical fiber in which a refractive index of a clad is reduced by holes. It is known that the holey fiber obtains an optical characteristic that cannot be obtained by a conventional optical fiber in which a refractive index of a clad is reduced by an impurity.

As described in Patent Literatures 1 through 4, the holey fiber is manufactured by the steps of (1) preparing a columnar base material (hereinafter, referred to as a "preform") made from silica glass, (2) forming, in the preform, through holes which are to be holes, and (3) drawing the preform in which the through holes have been formed.

The optical characteristic of the holey fiber is influenced by positions of the holes. Accordingly, it is important to form the through holes in predetermined appropriate positions in the preform in order to manufacture an optical fiber having a desired optical characteristic.

In the step (3), through holes extending in a direction vertical to end surfaces of the preform are formed by a drilling process. If a machine tool for forming the through holes has low machining accuracy, perforating positions of the through holes are gradually shifted as the perforating is proceeded even if the perforating is started from appropriate positions of one end surface. Accordingly, positions of the through holes are largely shifted at the other end surface, or a through hole is connected to another through hole in the middle of the preform. For this reason, after the through holes are formed, it is necessary to whether or not through holes are formed in respective appropriate positions.

The inspection as to whether or not through holes are formed in respective appropriate positions has been normally carried out by a method in which a preform is observed from an end surface by use of an optical microscope.

However, the conventional inspecting method by use of an optical microscope can inspect only forming positions of holes in the vicinity of an end surface of a preform. That is, the forming positions of the holes in the middle of end surfaces (at an arbitrary cross-section between both end surfaces) cannot be inspected. There is another method in which forming positions of through holes in the middle of a preform are estimated from (i) forming positions of holes in one end surface and (ii) forming positions of the holes in the other end surface. However, such estimation cannot accurately specify the forming positions of the holes in the middle of the end surfaces. In view of the circumstances, it is necessary to inspect which portion of a preform is suitable for manufacturing an optical fiber by cutting the preform in round slices in a case where forming positions of through holes in an end surface are largely shifted from respective appropriate positions. This inspection increases a manufacturing cost.

On the contrary, Patent Literature 5 discloses a method for inspecting whether or not through holes are formed in respective appropriate positions on the basis of an intensity distribution of forward scattered light which is generated by parallel light entering from a side surface of a preform.

CITATION LIST

Patent Literature

Patent Literature 1
Japanese Patent Application Publication, Tokukai, No. 2002-145634 A (Publication date: May 22, 2002)
Patent Literature 2
Japanese Patent Application Publication, Tokukai, No. 2002-249335 A (Publication date: Sep. 6, 2002)
Patent Literature 3
Japanese Patent Application Publication, Tokukai, No. 2002-293562 A (Publication date: Oct. 9, 2002)
Patent Literature 4
Japanese Patent Application Publication, Tokukai, No. 2006-160528 A (Publication date: Jun. 22, 2006)
Patent Literature 5
International Publication WO 2011/052541 (Publication date: May 5, 2011)

SUMMARY OF INVENTION

Technical Problem

The inspecting method described in Patent Literature 5 is superior, to conventional inspecting methods by use of an optical microscope, in that the inspecting method of Patent Literature 5 can determine whether or not through holes are formed in respective appropriate positions without destroying a preform. Note, however, that the inspecting method is desired to make further improvements in the following points.

That is, in a case of employing the inspecting method described in Patent Literature 5, it is necessary to cause high-intensity parallel light to enter a preform from a side surface of the preform in order to generate detectable forward scattered light. This costs money to manufacture an inspecting device and implement the inspecting method.

Even if an intensity distribution of the detectable forward scattered light is obtained by causing the high-intensity parallel light to enter the preform from the side surface of the preform, the intensity distribution of the forward scattered light is merely such one that has a dark portion corresponding to a shadow of a region which includes all through holes (e.g., in a case where the through holes are formed at respective six apexes of regular hexagon, the whole region becomes regular hexagon). It is therefore possible to precisely detect positional displacements of the through holes, which positional displacements may deform the region which includes all the through holes, such as (i) a displacement in which the through holes are formed so as to gather around a center and (ii) a displacement in which the through holes are formed so as to be away from the center. However, it has been difficult to precisely specify (i) positions of the through holes and (ii) a size of the through holes.

The present invention has been made in view of the aforementioned problem, and an object of the present invention is to provide (I) an inspecting device which can accurately confirm, without using high-intensity parallel light and destroying the preform, whether or not through holes are formed in respective appropriate positions in the middle of both end surfaces of a preform so that each of the through holes has an appropriate size, and (II) an inspecting method.

Solution to Problem

In order to attain the aforementioned object, an inspecting device in accordance with the present invention includes: detecting means for sequentially detecting an intensity distribution of transmitted light which (i) has entered a side surface of a columnar preform having through holes and (ii) has been transmitted through a center portion of the preform; rotating/moving means for (a) moving the preform so that the preform is rotated about a center axis of the preform, the center axis serving as a rotating axis, or (b) moving the detecting means so that the detecting means rotates around the preform; and calculating means for calculating a time series of a feature value from the intensity distribution of the transmitted light, which intensity distribution has been sequentially detected, the feature value having a value corresponding to at least one of (i) arrangement of the through holes and (ii) a size of each of the through holes.

In a case of forward scattered light, its intensity distribution has a dark portion corresponding to a shadow of a region which includes all the through holes. On the contrary, in a case of transmitted light, its intensity distribution has a dark portion corresponding to a shadow of one through hole. Conventionally, it has been difficult to specify (i) arrangement of the through holes or (ii) a size of the through holes on the basis of the time series of the feature value calculated from the intensity distribution of the forward scattered light. However, according to the arrangement, it is possible to precisely specify the through holes separately, i.e., to precisely specify the arrangement and the size. Furthermore, according to the arrangement, the inspecting device does not detect the intensity distribution of the forward scattered light, but detects the intensity distribution of the transmitted light, so that it is unnecessary to cause high-intensity parallel light to enter the preform, unlike a case of detecting the intensity distribution of the forward scattered light.

That is, according to the arrangement, it is possible to precisely inspect whether or not each of the through holes is formed in an appropriate position with an appropriate size, without (i) using high-intensity parallel light and (ii) destroying the preform.

In order to attain the aforementioned object, an inspecting method in accordance with the present invention includes the steps of: (A) sequentially detecting, by use of detecting means, an intensity distribution of transmitted light which (i) has entered a side surface of a columnar preform having through holes and (ii) has been transmitted through a center portion of the preform; (B) (a) moving the preform so that the preform is rotated about a center axis of the preform, the center axis serving as a rotating axis, or (b) moving the detecting means so that the detecting means rotates around the preform; (C) calculating a time series of a feature value from the intensity distribution of the transmitted light, which intensity distribution has been sequentially detected, the feature value having a value corresponding to at least one of (i) arrangement of the through holes and (ii) a size of each of the through holes; and (D) determining whether or not the at least one of (i) the arrangement of the through holes and (ii) the size of each of the through holes is appropriate on the basis of the time series of the feature value calculated in the step of (C).

According to the present invention, the inspecting method has an effect which is similar to that of the inspecting device of the present invention.

Further, a method for manufacturing an optical fiber in accordance with the present invention includes the steps of: (A) sequentially detecting, by use of detecting means, an intensity distribution of transmitted light which (i) has entered a side surface of a columnar preform having through holes and (ii) has been transmitted through a center portion of the preform; (B) (a) moving the preform so that the preform is rotated about a center axis of the preform, the center axis serving as a rotating axis, or (b) moving the detecting means so that the detecting means rotates around the preform; (C) calculating a time series of a feature value from the intensity distribution of the transmitted light, which intensity distribution has been sequentially detected, the feature value having a value corresponding to at least one of (i) arrangement of the through holes and (ii) a size of each of the through holes; and (D) determining whether or not the at least one of (i) the arrangement of the through holes and (ii) the size of each of the through holes is appropriate on the basis of the time series of the feature value calculated in the step of (C).

According to the present invention, the method for manufacturing an optical fiber has an effect which is similar to that of the inspecting method of the present invention.

Advantageous Effects of Invention

According to the present invention, it is possible to perform nondestructive inspection to precisely confirm whether or not through holes are formed in respective predetermined positions.

A top view of FIG. 3 is a cross-sectional view of a preform in which through holes are not formed, and a bottom view of FIG. 3 is a graph showing an intensity distribution of transmitted light obtained when the preform in which the through holes are not formed is irradiated with inspecting light.

A top view of FIG. 4 is a cross-sectional view of a preform in which through holes are formed in respective appropriate positions, and a bottom view of FIG. 4 is a graph showing an intensity distribution of transmitted light obtained when the preform in which the through holes are formed in the respective appropriate positions is irradiated with inspecting light.

A top view of FIG. 5 is a cross-sectional view of a preform in which through holes are formed in respective appropriate positions, and a bottom view of FIG. 5 is a graph showing an intensity distribution of transmitted light obtained when the preform in which the through holes are formed in the respective appropriate positions is irradiated with inspecting light.

Figure 6:
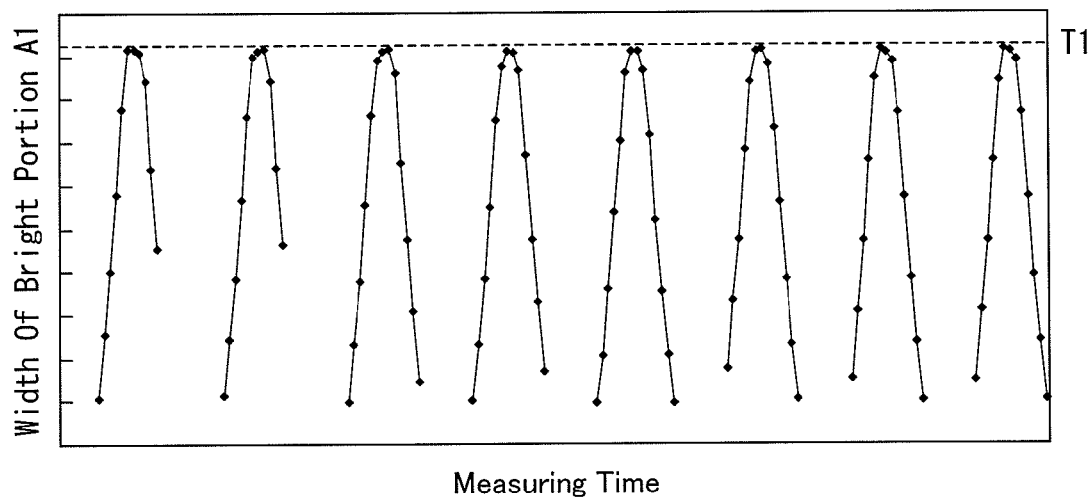

FIG. 6 is a graph showing a time series of a width of a bright portion obtained from an ideal preform in which all through holes are formed in respective appropriate positions.

Figure 7:
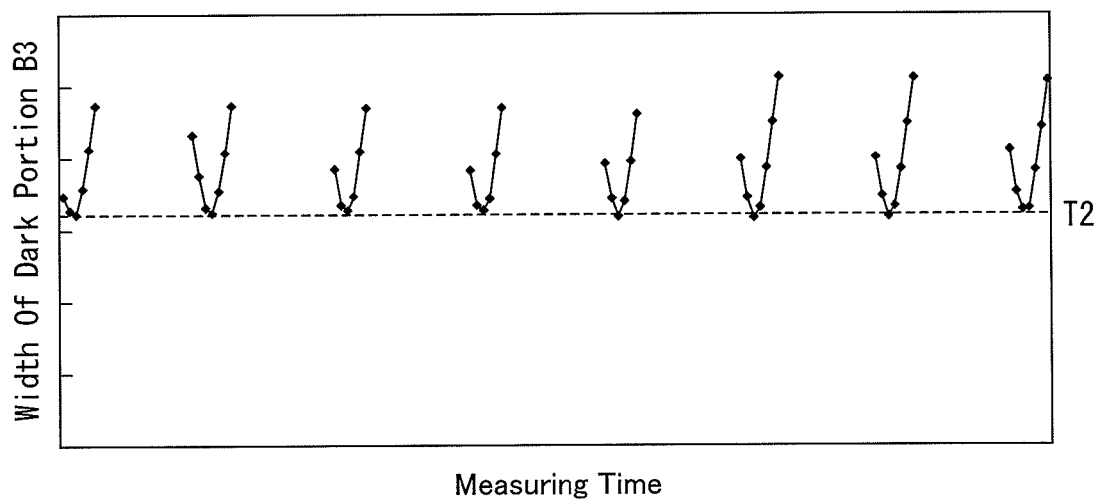

FIG. 7 is a graph showing a time series of a width of a dark portion obtained from an ideal preform in which each of the through holes is formed with an appropriate width.

FIG. 8 is a table showing intervals between adjacent through holes, which intervals were obtained from a time series of a width of a bright portion.

FIG. 9 is a table showing intervals between adjacent through holes, which intervals were actually measured.

Figure 10:
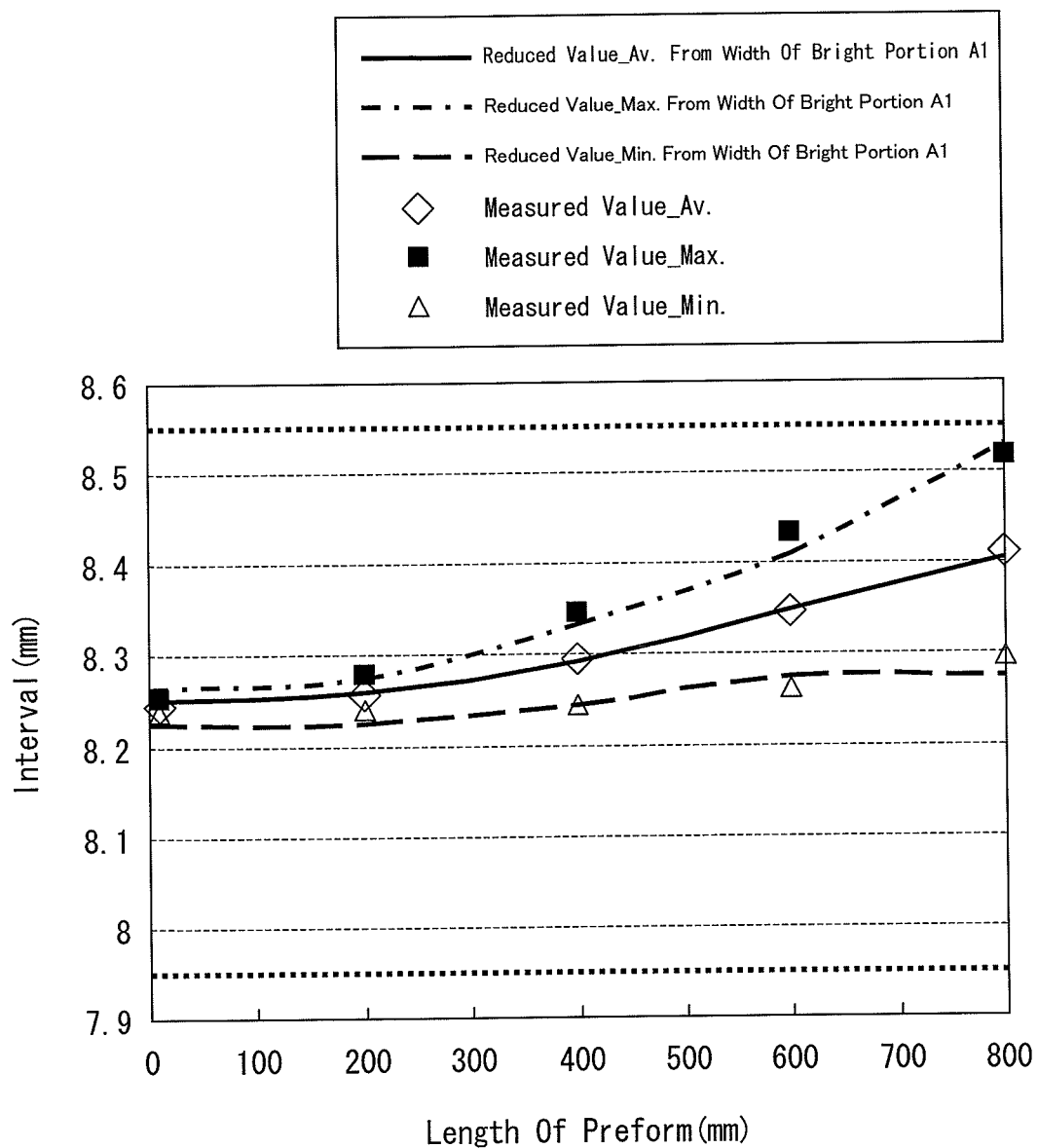

FIG. 10 is a graph showing measured values shown in FIGS. 8 and 9.

FIG. 11 is a table showing widths of respective through holes obtained from a time series of a width of a dark portion.

FIG. 12 is a table showing widths of respective through holes, which widths were actually measured.

Figure 13:
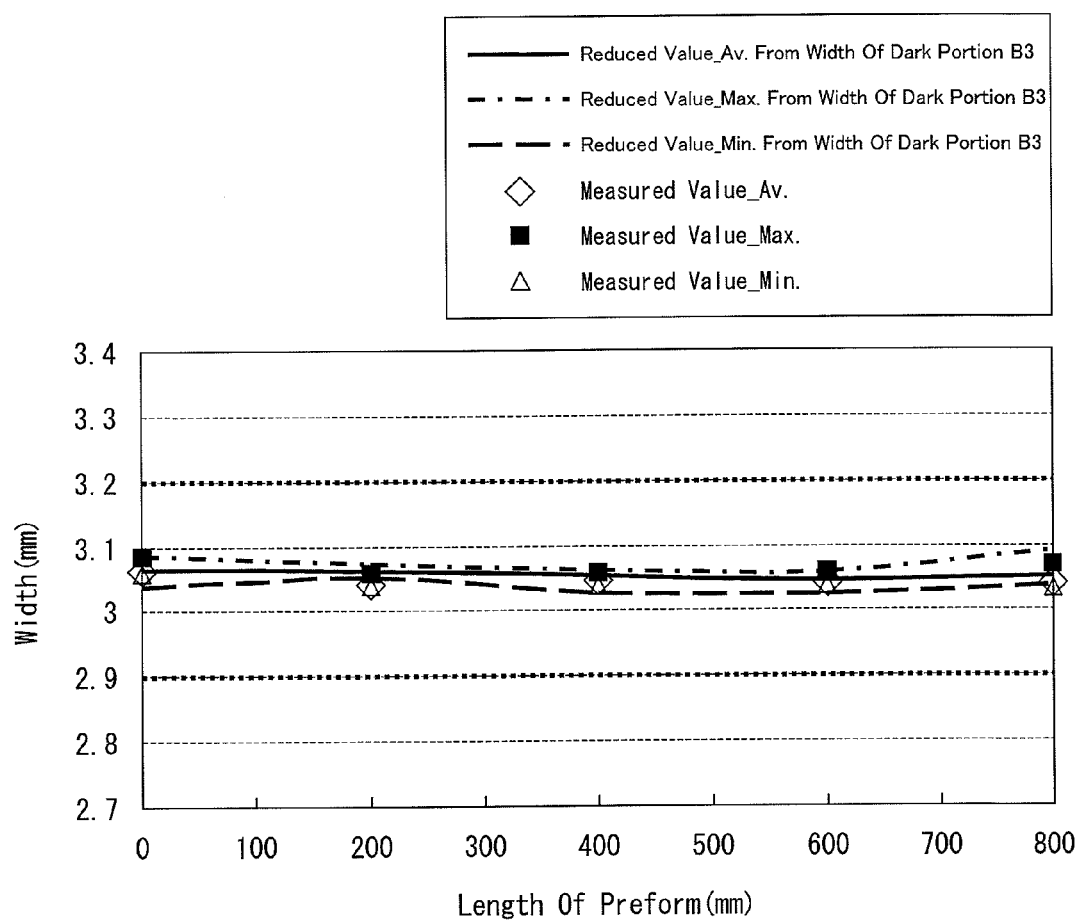

FIG. 13 is a graph showing measured values (average values, maximum values, and minimum values) shown in FIGS. 11 and 12.

Figure 14:
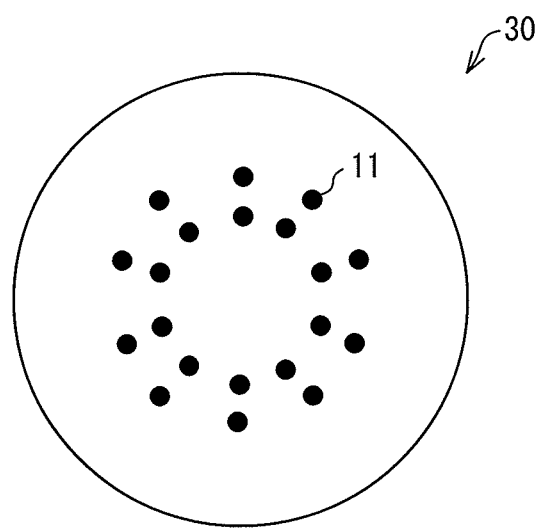

FIG. 14 is a cross-sectional view of a preform which is different from a preform of this example in terms of positions of through holes.

Figure 15:
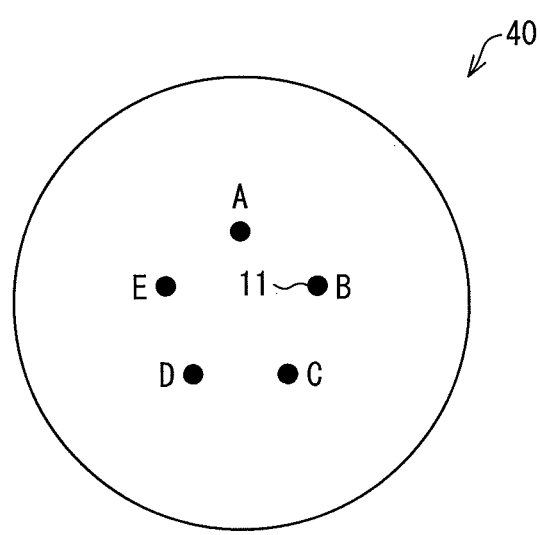

FIG. 15 is a cross-sectional view of a preform which is different from a preform of this example in terms of positions of through holes.

DESCRIPTION OF EMBODIMENTS

One embodiment of the present invention will be described below with reference to the drawings. Note that an "optical fiber" described in the Embodiment described below indicates an optical fiber in which at least one hole is formed in a direction of a center axis of the optical fiber, unless otherwise noted. Further, a "preform" described in this embodiment indicates a preform which is a base material of an optical material in which at least one hole is formed, that is, a preform in which at least one through hole is formed, unless otherwise noted. Note that the preform can contain silica glass etc. as a main component, and can contain germanium, fluorine, or the like as a dopant.

(Structure of Inspecting Device)

Figure 1:
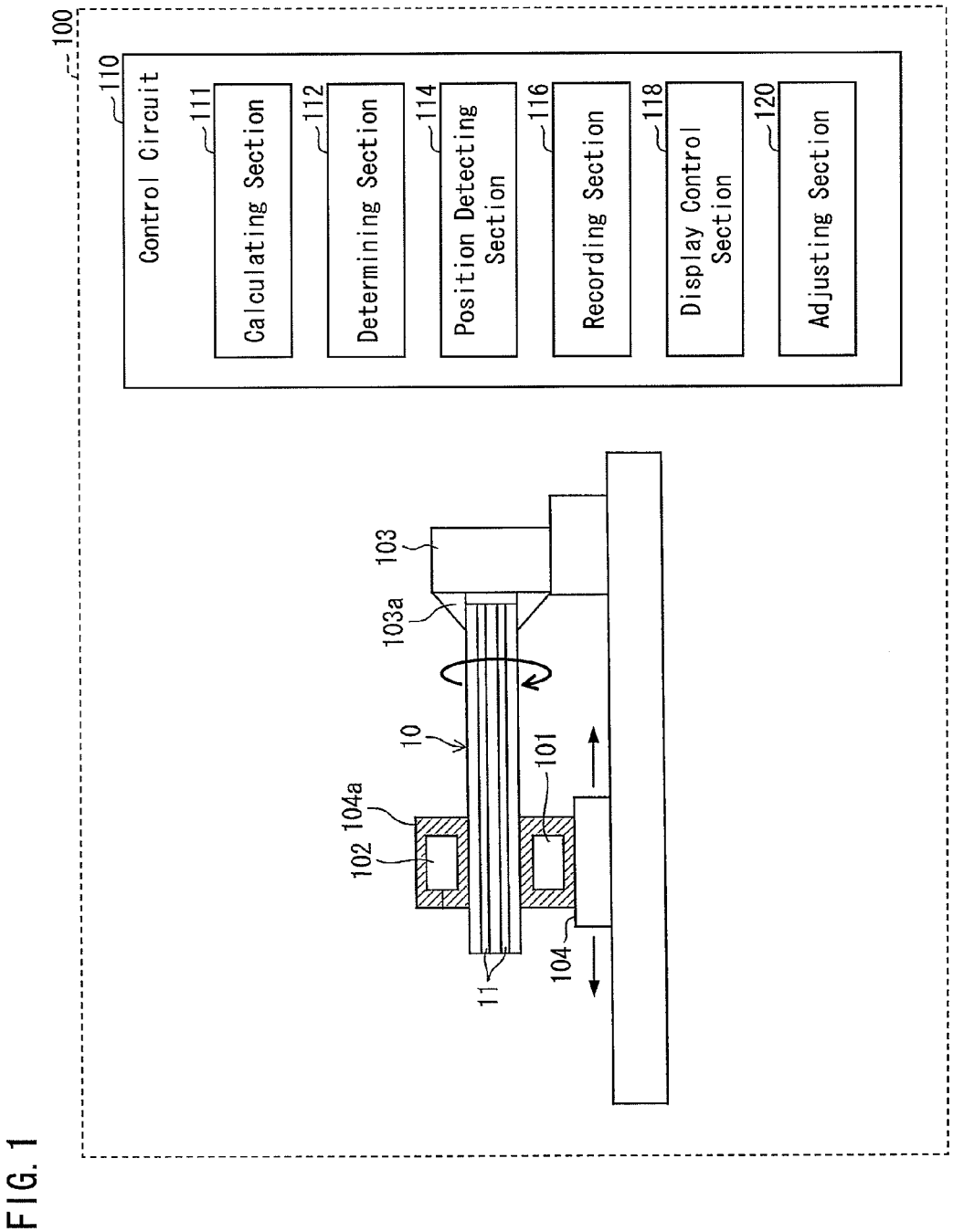
FIG. 1 is a view illustrating a schematic structure of an inspecting device in accordance with this embodiment.

The following description will discuss a structure of an inspecting device 100 of this embodiment. FIG. 1 is a view illustrating a schematic structure of an inspecting device 100 of this embodiment.

The inspecting device 100 illustrated in FIG. 1 is a device for inspecting a preform in which through holes are formed in manufacturing steps of an optical fiber. Specifically, the inspecting device 100 is a device for inspecting whether or not each of the through holes is formed in a predetermined appropriate position with a predetermined appropriate size.

As illustrated in FIG. 1, the inspecting device 100 includes a light source 101, a detector (detecting means) 102, a rotating mechanism (rotating/moving means) 103, a parallel moving mechanism (parallel moving means) 104, and a control circuit 110.

The light source 101 is a device which irradiates, with inspecting light, a side surface of a preform 10. Examples of the light source 101 encompass a laser irradiating device or LED (light emitting diode). Some inspecting light emitted from the light source 101 and entered a center portion of the preform 10 become transmitted light which is transmitted through the preform 10 and is emitted from a side opposite to a side on which the light source 101 of the preform 10 is provided. Then, the transmitted light is detected by the detector 102, and intensity of the transmitted light is indicated in its intensity distribution. The transmitted light thus generated is expressed as the "transmitted light of the preform 10" in the specification of the present invention.

Note that some inspecting light emitted from the light source 101 and entered a portion other than the center portion of the preform reflects on a surface of the preform 10, that is, is not transmitted through the preform 10. Further, part of the inspecting light, which has been emitted from the light source 101 and has not entered the preform 10, becomes passing light traveling outside the preform 10. The passing light traveling outside the preform 10 as described above is also detected by the detector (detecting means) 102, and intensity of the passing light is indicated as an intensity distribution of the transmitted light. For this reason, the passing light thus generated is expressed as "transmitted light of the preform 10" for the sake of convenience in the specification of the present invention.

The detector 102 is means for sequentially detecting the intensity distribution of the transmitted light of the preform 10. More specifically, the detector 102 is means for sequentially detecting, in a plane which (i) is positioned on the side opposite to the side on which the light source 101 of the preform 10 is provided and (ii) is orthogonal to the inspecting light emitted from the light source 101, the intensity distribution on a straight line orthogonal to an orthographic projection of the center axis of the preform 10. It is possible to achieve such detector 102 by placing, for example, CCD (charge coupled device) line sensors along the straight line. Alternatively, it is possible to employ an arrangement in which the intensity distribution on the straight line is scanned by use of a CCD point sensor which moves along the straight line.

The rotating mechanism 103 is means for rotating the preform 10, which is held by a holding section 103a, about a center axis (of the preform 10) as a rotating axis. By rotating the preform 10 by use of the rotating mechanism 103, it is possible to sequentially detect the transmitted light of the preform 10 transmitted from various directions. Similarly, it is also possible to employ a structure in which the light source 101 and the detector 102 are moved so as to rotate around the preform 10, instead of employing the structure in which the preform 10 is rotated by use of the rotating mechanism 103, as in this embodiment.

The parallel moving mechanism 104 is means for parallel moving the light source 101 and the detector 102, held by a supporting section 104a, in a direction of the center axis of the preform 10. It is possible to detect cross-sections of the transmitted light of the preform 10 in various directions by parallel moving the light source 101 and the detector 102 by use of the parallel moving mechanism 104 while rotating the preform 10 by use of the rotating mechanism 103. Similarly, it is possible to employ a structure in which the preform 10 is moved in the direction of the center axis of the preform 10, instead of employing the structure in which the light source 101 and the detector 102 are parallel moved in the direction of the center axis of the preform 10 by use of the parallel moving mechanism 104, as in this embodiment.

The control circuit 110 controls sections of the inspecting device 100. The control circuit 110 includes a calculating section 111 (calculating means), a determining section 112 (determining means), a position detecting section 114, a recording section 116, a display control section 118, and an adjusting section 120.

The calculating section 111 calculates a time series of a feature value of the transmitted light from the intensity distribution of the transmitted light of the preform 10, which intensity distribution has been sequentially detected by the detector 102. In particular, the calculating section 111 of this embodiment calculates a time series of a width of a bright portion which is formed at a center of the intensity distribution, taking the width of the bright portion as a feature value. Further, the calculating section 111 of this embodiment calculates a time series of a width of a dark portion between two bright portions which are formed in the vicinity of the center of the intensity distribution, taking the width of the dark portion as a feature value.

The calculating section 111 of this embodiment can also calculate a time series of a ratio of (i) an interval (first interval) between a first bright portion and a second bright portion to (ii) an interval (second interval) between the first bright portion and a third portion, taking the ratio as a feature value. In the above, the "first bright portion" indicates a bright portion formed at the center of the intensity distribution by the transmitted light which has been transmitted through the center portion of the preform 10. Further, the "second bright portion" and the "third bright portion" indicate bright portions formed in both ends of the intensity distribution by passing light which has traveled outside the preform 10.

On the basis of the time series of the width of the bright portion calculated by the calculating section 111, the determining section 112 detects whether or not the through holes 11 are formed in appropriate intervals. Also, on the basis of the time series of the width of the dark portion calculated by the calculating section 111, the determining section 112 detects whether or not each of the through holes 11 is formed with an appropriate size (diameter).

The position detecting section 114 detects an inspecting position in the center axis of the preform 10. Specifically, the position detecting section 114 detects positions of the light source 101 and the detector 102 with respect to the preform 10.

The recording section 116 records, on a recording medium (such as a memory), a result of detection carried out by the determining section 112 while mapping the result to the inspecting position detected by the position detecting section 114. By referring information recorded on the recording medium, a tester can determine whether or not the positions and the sizes of the through holes 11 in the cross-sections of the preform 10 are appropriate.

The display control section 118 causes a display (not illustrated) included in the inspecting device 100 to display various kinds of information relating to inspection of the preform 10. Examples of the information to be displayed to the display encompass (i) intensity distribution of the transmitted light of the preform 10, (ii) results of the calculation (e.g., the time series of the width of the bright portion and the time series of the width of the dark portion) carried out by the calculating section 111, and (iii) results of the detection (e.g., positions of the through holes 11, whether or not the through holes 11 are formed in respective appropriate positions, size of each of the through holes 11, and whether or not each of the through holes 11 is formed with an appropriate size) carried out by the determining section 112.

The adjusting section 120 adjusts intensity of inspecting light emitted from the light source 101. A range in which the inspecting light is transmitted through the preform 10 (hereinafter, also referred to as a "transmitted range of the inspecting light") differs depending on (i) intensity of the inspecting light emitted from the light source 101 and (ii) features (e.g., a curvature of a surface of the preform and a material of the preform) of the preform 10. Further, a preferable transmitted range of the inspecting light differs depending on features (e.g., positions of the through holes, size of each of the through holes, an interval between the through holes) of the through holes 11 formed in the preform 10.

In view of the circumstances, the intensity of the inspecting light is adjusted by the adjusting section 120, so that an appropriate transmitted range of the inspecting light is set, by the inspecting device 100 of this embodiment, in accordance with the features of (i) the preform 10 and (ii) the through holes.

Examples of a method for adjusting the intensity of the inspecting light encompass a method in which optimal intensity is set so that the transmitted range of the inspecting light falls within a desired range by adjusting the intensity of the inspecting light while monitoring the transmitted range of the inspecting light. Alternatively, in a case where the intensity of the inspecting light, which causes the transmitted range of the inspecting light to fall within a desired range, is known in advance, it is possible to set the intensity without the monitoring.

(Intensity Distribution of Transmitted Light Obtained by Inspecting Device 100)

The following description will discuss an intensity distribution of transmitted light obtained by the inspecting device 100.

Figure 2:
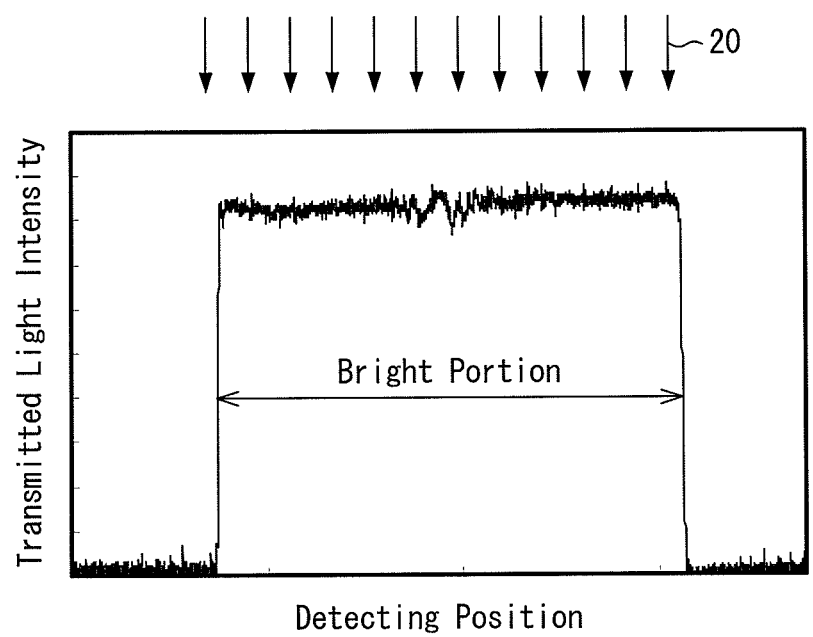
FIG. 2 is a graph showing an intensity distribution of transmitted light obtained when inspecting light is emitted in a state in which a preform is not placed.

FIG. 2 is a graph showing an intensity distribution of transmitted light obtained when inspecting light 20 is emitted in a state in which a preform is not placed.

In a case where a preform to be inspected is not placed on the inspecting device 100, the inspecting light 20 emitted from the light source 101 is received, with very slight attenuation, by a receiving section 102 provided so as to face the light source 101.

As shown in FIG. 2, in the intensity distribution of the transmitted light detected by the detector 102, a region which corresponds to an irradiation range of the inspecting light 20 emitted from the light source 101 is a portion (hereinafter, referred to as a "bright portion") whose intensity is much brighter than reference intensity.

The specification of the present invention employs, as an inspecting method, a method for irradiating a preform with the inspecting light 20 so that the inspecting light 20 scans a whole cross-section of the preform. Accordingly, the irradiation range of the inspecting light 20 should be larger than a diameter of the preform to be inspected. In addition, when inspecting a preform, the preform should be placed on the inspecting device 100 so as to be disposed within the irradiation range of the inspecting light 20.

The inspecting device 100 can include adjusting means for adjusting the irradiation range of the inspecting light 20 in order to reduce wasted inspecting light 20. This makes it possible to appropriately set the irradiation range of the inspecting light 20 in accordance with the diameter of the preform.

Note that the reason why the irradiation range of the inspecting light 20 should be larger than the diameter of the preform is that positions of both end portions of the preform in radial direction of the preform are set to be recognized from the intensity distribution of the transmitted light transmitted through the preform.

Accordingly, if there is no need to recognize positions of the both end portions, the irradiation range of the inspecting light 20 can be equal to or smaller than the diameter of the preform.

A top view of FIG. 3 is a cross-sectional view of a preform 10 in which through holes are not formed. A bottom view of FIG. 3 is a graph showing an intensity distribution of transmitted light obtained when the preform 10 in which a through hole is not formed is irradiated with inspecting light 20.

As illustrated in the top view of FIG. 3, part of inspecting light 20 emitted from the light source 101 irradiates a center of the preform 10 and a vicinity of the center thereof (hereinafter, the center and the vicinity of the center are collectively referred to as a "center portion of the preform 10"). This part of the inspecting light 20 has a relatively small angle of incidence to a surface of the preform 10, whereby this part of the inspecting light 20 are hardly refracted or reflected on the surface of the preform 10. Accordingly, this part of the inspecting light 20 is mostly transmitted through the preform 10 and are detected by the detecting section 102.

Meanwhile, another part of the inspecting light 20 emitted from the light source 101 irradiates portions (hereinafter, referred to as "both end portions of the preform 10") other than the center portion of the preform 10. The another part of the inspecting light 20 has a relatively large angle of incidence of the inspecting light 20 to the surface of the preform 10, whereby the another part of the inspecting light 20 is refracted or reflected. Accordingly, the another part of the inspecting light 20 is mostly not transmitted, and is not detected by the detecting section 102.

As a result, as illustrated in the bottom view of FIG. 3, the intensity distribution of the transmitted light of the preform 10 has (i) a bright portion in a position corresponding to the center portion of the preform 10 and (ii) dark portions in positions corresponding to the both end portions of the preform 10. In this case, the dark portions indicate dark portions whose intensity is smaller than the reference intensity, which dark portions are generated in positions corresponding to the respective both end portions of the preform 10.

For example, in the intensity distribution illustrated in the bottom view of FIG. 3, a bright portion A1 is generated in a position corresponding to the center portion of the preform 10, meanwhile, a dark portion B1 is generated on a left side of the bright portion A1 and a dark portion B2 is generated on a right side of the bright portion A1.

Furthermore, still another part of the inspecting light 20 emitted from the light source 101 irradiates the outside of the preform 10. The still another part of the inspecting light naturally travels outside the preform 10 without being refracted and reflected by the preform 10, and is then detected by the detector 102.

As a result, the intensity distribution has other bright portions in positions corresponding to external portions of the respective end portions of the preform 10.

For example, in the intensity distribution illustrated in the bottom view of FIG. 3, a bright portion A2 is generated in a portion corresponding to one external portion of the preform 10, meanwhile, a bright portion A3 is generated in a portion corresponding to the other external portion of the preform 10.

A top view of FIG. 4 is a cross-sectional view of a preform 10 in which through holes are formed in respective appropriate positions, and a bottom view of FIG. 4 is a graph showing an intensity distribution of transmitted light obtained when the preform 10 (in which the through holes are formed in the respective appropriate positions) is irradiated with inspecting light 20.

The preform 10 illustrated in FIG. 4 is such that ten through holes 11 are formed on a concentric circle at regular intervals. In particular, FIG. 4 shows a cross-section of the preform 10 and the intensity distribution when two through holes are adjacent to each other on a path of the inspecting light 20 entered the center portion of the preform 10 in a direction orthogonal to a traveling direction of the inspecting light 20.

This example of FIG. 4 is similar to the inspecting light 20 exemplified in FIG. 3 in that (I) the inspecting light 20 which has been emitted from the light source 101 and has irradiated the both end portions of the preform 10 is hardly detected by the detector 102 and (II) the inspecting light 20 which has traveled outside the preform is mostly detected by the detector 102.

Accordingly, in the example of FIG. 4, the intensity distribution of the transmitted light of the preform 10 is similar to the intensity distribution of FIG. 3 in that, as illustrated in FIG. 4, the intensity distribution has (i) the bright portion A1 in a portion corresponding to a center portion of the preform 10, (ii) dark portions B1 and B2 in portions corresponding to the both end portions, respectively, of the preform 10, and (iii) bright portions A2 and A3 in portions corresponding to external portions, respectively, of the both end portions of the preform 10.

Meanwhile, part of the inspecting light 20 having entered the preform 10 and having irradiated the center portion of the preform 10 reaches the through holes 11 provided on a path of the inspecting light 20, and is then refracted or reflected on surfaces of the through holes 11. Accordingly, the part of the light beams, entering the center portion of the preform 10, is not transmitted through the preform 10, so that the part of the light is not detected by the detector 102.

When comparing the intensity distribution of FIG. 3 and the intensity distribution of FIG. 4 with each other, it is clear that the width of the bright portion A1 in the intensity distribution of FIG. 4 is smaller than that of FIG. 3.

In a case of FIG. 4, positions of edge (turning points of the intensity) of the bright portion A1 in the intensity distribution is determined by a position of a through hole 11. This allows the determining section 112 to easily determine, from the position of the edge of the bright portion A1, the position of the through hole 11.

Further, the width of the bright portion A1 is determined by an interval between two through holes 11 adjacent to each other. This allows the determining section 112 to easily determine, from the width of the bright portion A1 in the intensity distribution, the interval between the two through holes 11.

Note that the width of the bright portion A1 becomes maximum when two through holes 11 are aligned so as to be adjacent to each other, in the direction orthogonal to the traveling direction of the inspecting light 20, on the path of the inspecting light 20 entered the center portion of the preform 10 as illustrated in FIG. 4. That is, it can be said that a maximum width of the bright portion A indicates the most accurate interval between two through holes 11 adjacent to each other.

By sampling the intensity distribution while rotating the preform 10, it is possible that the determining section 112 easily determines, from a maximum width of the bright portion A, an interval between the two adjacent through holes 11.

In order to measure an interval between through holes 11, the irradiation range of the inspecting light 20 should be larger than at least an ideal interval between through holes 11. Note, however, that, if the irradiation range is unnecessarily increased, other through holes 11 etc. may influence a result of measurement. Accordingly, the irradiation range should be set appropriately. The inspecting device 100 of this embodiment includes the adjusting section 120, so that the inspecting device 100 can appropriately set the irradiation range of the inspecting light.

A top view of FIG. 5 is a cross-sectional view of a preform 10 in which through holes are formed in respective appropriate positions, and a bottom view of FIG. 5 is a graph showing an intensity distribution of transmitted light obtained when the preform 10 (in which the through holes are formed in the respective appropriate positions) is irradiated with inspecting light 20.

Specifically, FIG. 5 is views illustrating the cross-section of the preform 10 and the intensity distribution obtained when the through holes 11 are provided on a path of the inspecting light 20 (which (i) has entered the center portion of the preform and (ii) has been transmitted through a center axis of the preform 10) by rotating the preform 10 illustrated in FIG. 4.

This example of FIG. 5 is similar to the inspecting light 20 exemplified in FIGS. 3 and 4 in that (I) the inspecting light 20 which has been emitted from the light source 101 and has irradiated the both end portions of the preform 10 is hardly detected by the detector 102 and (II) the inspecting light 20 which has traveled outside the preform is mostly detected by the detector 102.

Accordingly, in the example of FIG. 5, the intensity distribution of the transmitted light of the preform 10 is similar to the intensity distribution of each of FIGS. 3 and 4 in that, as illustrated in FIG. 5, the intensity distribution has (i) the bright portion A1 in a portion corresponding to a center portion of the preform 10, (ii) dark portions B1 and B2 in portions corresponding to the both end portions, respectively, of the preform 10, and (iii) bright portions A2 and A3 in portions corresponding to external portions, respectively, of the both end portions of the preform 10.

Meanwhile, part of the inspecting light 20 having been entered the center portion of the preform 10 and having been transmitted on the center axis of the preform 10 is emitted and irradiates the through holes 11 provided on a path of the inspecting light 20 in the preform, and is then refracted or reflected on surfaces of the through holes 11. Accordingly, the part of the light irradiating the center axis of the preform 10 are completely not transmitted through the preform 10, so that the part of the inspecting light 20 is not detected by the detector 102.

When comparing the intensity distribution of FIG. 3 and the intensity distribution of FIG. 5, it is clear that a dark portion B3 is generated in a center portion (i.e., a portion between two bright portions) of the bright portion A1 in the intensity distribution of FIG. 5.

In a case of FIG. 5, a width of the dark portion B3 is determined by a size (diameter) of each of the through holes 11. This allows the determining section 112 to easily determine, from the width of the dark portion B3 in the intensity distribution, the size of each of the through holes 11.

As illustrated in FIG. 5, in a case where two through holes 11 face each other on the path of the inspecting light 20 (which enters the preform 10) while sandwiching the center axis of the preform 10, the width of the dark portion B3 becomes minimum when the through holes 11 are provided on the path of the inspecting light 20 transmitted on the center axis. That is, it can be said that the minimum width of the dark portion B3 indicates the most accurate size of each of the through holes 11.

By sampling the intensity distribution while rotating the preform 10, it is possible that the determining section 112 easily determines, from a minimum width of the bright portion B3, an interval between the two adjacent through holes 11.

(Method for Determining Whether or Not Through Holes are Provided in Respective Appropriate Positions)

The following description will discuss a method for determining, on the basis of a time series of a width of a bright portion A1, whether or not through holes are provided in respective appropriate positions. FIG. 6 is a graph showing a time series of a width of a bright portion A1 of an ideal preform 10 in which all through holes 11 are provided in respective appropriate positions.

The inspecting device 100 of this embodiment can obtain intensity distribution in such a manner that transmitted light of the preform 10, transmitted from various directions, are detected by rotating the preform 10 by use of the rotating mechanism 103. Further, the inspecting device 100 can obtain, from the widths of the bright portions A1 of intensity distributions, the time series of the width of the bright portion A1 shown in FIG. 6.

As shown in the graph of FIG. 6, in a case where the plurality of through holes 11 are provided in predetermined appropriate positions, all the maximum values become substantially identical to a threshold value T1 in a time series of the width of the bright portion A1 obtained when the preform 10 is rotated once.

In a case where an interval between two through holes 11 adjacent to each other is larger than a predetermined interval, one of the maximum values becomes larger than the threshold value T1.

Meanwhile, in a case where an interval two through holes 11 adjacent to each other is smaller than the predetermined interval, one of the maximum values becomes smaller than the threshold value T1.

For example, the determining section 112 can determine whether or not all the through holes 11 are formed in respective appropriate positions in such a manner that (1) all the maximum values are extracted from the time series and (2) the respective maximum values thus extracted are compared with a threshold value T1 which has been stored in a memory in advance.

For example, in a case where, in such determination process, all the maximum values are substantially equal to the threshold value T1, the determining section 112 determines that "all through holes 11 are formed in respective appropriate positions".

Consider that, although a positional relationship between the through holes 11 is appropriate, a center of the plurality of through holes 11 are shifted from a center axis of the preform 10. In this case, the aforementioned method by use of the determining section 112 sometimes cannot detect such shift.

In view of the circumstances, the determining section 112 can determine whether or not the through holes 11 are shifted from the center axis on the basis of a time series of a ratio of (i) a dark portion B1 (interval between a first bright portion and a second bright portion) to (ii) a dark portion B2 (interval of the first bright portion and a third bright portion). The ratio is obtained from intensity distributions obtained by rotating the preform 10 by use of the rotating mechanism 103.

For example, the determining section 112 can determine that "through holes 11 are not shifted from the center axis" when the ratio of the dark portion B1 to the dark portion B2 is constant in the time series, and can determine that "through holes are shifted from the center axis" when the ratio of the dark portion B1 to the dark portion B2 is not constant in the time series.

(Method of Determining Whether or Not Through Hole is Formed With an Appropriate Size)

The following describes a method of determining whether or not each of the through holes is formed with a predetermined appropriate size (diameter), which method is performed by the determining section 112 on the basis of the time series of the width of the dark portion B3. FIG. 7 is a graph showing the time series of the width of the dark portion B3 obtained by an ideal preform 10 in which each of the through holes 11 is formed with an appropriate size.

The inspecting device 100 of this embodiment causes the rotating mechanism 103 to rotate the preform 10, and detects transmitted light of the preform 10, which are transmitted from respective directions, thereby obtaining an intensity distribution of the transmitted light. Further, it is possible to obtain a time series of the width of the dark portion B3 (see FIG. 7) from the widths of the dark portion B3 of the intensity distributions.

As shown in the graph of FIG. 7, in a case where each of the plurality of through holes 11 is formed to have a predetermined appropriate size in the preform 10, a minimum value of each of the through holes is substantially equal to a predetermined threshold value T2 in the time series of the width of the dark portion B3, which time series is obtained when the preform 10 is rotated once.

Meanwhile, in a case where one of the plurality of through hoes 11 is formed with a size larger than the predetermined appropriate size, one minimum value becomes larger than the threshold T2.

Further, in a case where, among the plurality of through holes 11, through holes 11 facing each other via the center axis of the preform 10 are formed so as to be smaller than the predetermined appropriated size, any one of minimum values becomes smaller than the threshold value T2 in the time series.

For example, the determining section 112 can determine whether or not each of the through holes 11 are formed with an appropriate size in such a manner that (1) all the minimum values are extracted from the time series and (2) the respective maximum values thus extracted are compared with the threshold value T2 which has been stored in a memory in advance.

For example, in a case where, in the determination process, all the minimum values are substantially equal to the threshold value T2, the determining section 112 determines that "each of the through holes 11 is formed with an appropriate size".

EXAMPLE

The embodiment of the present invention will be discussed in detail by the following Example. As a matter of course, the present invention is not limited to the following Example, and can be variously changed from the Example in detail.

(Inspecting Procedure)

This example employed a preform 10 (outer diameter of 80 mm, length of 800 mm) in which eight through holes were formed so as to be formed on a concentric circle, and respective through holes adjacent to each other are provided at an interval of 8.25 mm. Each of the eight through holes (diameter of 3 mm) penetrates from one cross-section to the other cross-section.

A position and a size of each of the through holes 11 were inspected as described in the following procedure by use of the inspecting device 100 of this embodiment, and effectiveness of the inspecting device 100 was confirmed.

This example employed a laser irradiation device as the light source 101 and a so-called laser scanning method. The laser scanning method is a method in which (i) the light source 101 (laser irradiation device) irradiated the preform 101 with inspecting light 20 (laser) while irradiation positions were sequentially transited in a radial direction of the preform 10, and, (ii) while detecting positions were sequentially transited in the radial direction of the preform 10 in accordance with the irradiation positions, transmitted light of the preform 10 was sequentially detected by the detector 102. The inspecting device 100 calculates widths of bright portions and dark portions on the basis of a scanning speed and a scanning time of a laser scanning by use of a preset correlation equation.

Note that, in this example, the number of revolution of the preform 10 in the following procedure was set to 0.3 rpm. A sampling cycle performed by the detector 102 was set to 1 millisecond. A speed in which a parallel moving mechanism 104 moves the light source 101 and the detector 102 was set to 0.1 mm/min, and the scanning speed of the laser scanning was set to 400 mm/msec.

(1) Intensity distributions in various directions were obtained such that (i) the preform 10 was irradiated with the inspecting light 20 while the preform 10 was rotated by the inspecting device 100 and (ii) intensities of the transmitted light of the preform 10 were detected. Then, from those intensity distributions, a time series of a width of a bright portion A1 and a time series of a width of a dark portion B3 were obtained.

(2) Individual intervals between adjacent through holes 11, were determined on the basis of the time series of the width of the bright portion A1. Specifically, each of the intervals between the adjacent through holes 11 was calculated from a maximum value in the time series of the width of the bright portion A1. Simultaneously, a minimum interval, a maximum interval, and an average interval of the intervals of the through holes 11 were calculated.

(3) Sizes of the respective through holes 11 were determined on the basis of the time series of the width of the dark portion B3. Specifically, the sizes of the through holes 11 were calculated from respective minimum values in the time series of the width of the dark portion B3. Simultaneously, a minimum size, a maximum size, and an average size of the through holes 11 were calculated.

(4) The light source 101 and the detector 102 were moved, by the parallel moving mechanism 104, to a plurality of inspecting positions (in this example, positions of 10 mm, 200 mm, 400 mm, 600 mm, and 800 mm away from the one cross-section of the preform serve as inspecting positions) which are provided arbitrarily in a direction of the length of the preform 10, and the steps (1) through (3) were carried out in each of the plurality of inspecting positions.

(5) The preform 10 was cut at the inspecting positions, and (i) intervals between adjacent through holes 11 and (ii) widths of the through holes 11 in each cross-section were measured by use of a three-dimensional coordinate measuring machine.

(6) The intervals between adjacent through holes 11, which intervals were obtained from the time series of the width of the bright portion A1, and intervals between adjacent through holes 11, which intervals were actually measured, were compared with each other.

(7) The width of the each of the through holes 11, which width was obtained from the time series of the width of the dark portion B3, and a width of the each of the through holes 11, which width was actually measured, were compared with each other.

(Results of Inspection)

FIG. 8 is a table showing intervals between adjacent through holes 11, which intervals were obtained from the time series of the width of the bright portion A1. FIG. 9 is a table showing intervals between adjacent through holes 11, which intervals were actually measured.

As is clearly from FIGS. 8 and 9, a maximum error of (i) each of the intervals obtained by the inspecting device 100 and (ii) a corresponding one of the intervals obtained by actual measurement is merely 0.02 mm. From the above, it was confirmed that employing, as a method for measuring the intervals between adjacent through holes 11, an inspecting method by use of the inspecting device 100 which has been described in this embodiment was greatly effective.

FIG. 10 is a graph showing measured values (average values, maximum values, and minimum values) shown in FIGS. 8 and 9. The horizontal axis of the graph of FIG. 10 indicates a position of the preform 10 in a direction of the length of the preform 10, and the vertical axis indicates an interval between adjacent through holes 11.

It can be understood again from the graph shown in FIG. 10 that (i) an average interval, a maximum interval, and a minimum interval of the intervals, obtained by the inspecting device 100, and (ii) an average interval, a maximum interval, and a minimum interval of the intervals, obtained by actual measurement, are substantially equal to each other, that is, an almost no error occurs between them.

As is clear from the graph of FIG. 10, the intervals between the through holes 11 increase as a position of the preform 10 is moved away in the direction of the length of the preform 10. The inspecting device 100 may be configured to present such graph to a user by, for example, causing (i) a display to display the graph or (ii) a printer to print out the graph, thereby allowing the user to easily grasp positions of the through holes 11 in the preform 10.

Further, the graph of FIG. 10 shows upper and lower limits of the threshold. The upper and lower limits of the threshold are preset to the inspecting device 100. For example, the determining section 112 of the inspecting device 100 can determine whether or not each of the through holes 11 is formed in an appropriate position depending on whether or not the individual intervals between adjacent through holes 11 fall within the upper and lower thresholds. The inspecting device 100 may be configured to present such graph to a user by, for example, causing (i) a display to display such results of determination or (ii) a printer to print out the graph, thereby allowing the user to easily grasp whether or not each of the plurality of through holes 11 is formed in an appropriate position of the preform 10.

Note that the determining section 112 can determine whether or not each of the plurality of through holes 11 in the preform 10 is formed in an appropriate position depending on whether or not the average interval, the maximum interval, or the minimum interval of intervals between the through holes 11 fall within the upper and lower thresholds.

FIG. 11 is a table showing a size of the through holes 11 obtained from the time series of the width of the dark portion B3. FIG. 12 is a table showing a size of the through holes 11 obtained by actual measurement.

As is clearly from FIGS. 11 and 12, a maximum error of (i) a size of the through holes 11 obtained by the inspecting device 100 and (ii) a corresponding size obtained by actual measurement is merely 0.02 mm. From the above, it was confirmed that employing, as a method for measuring the sizes of the through holes 11, an inspecting method by use of the inspecting device 100 which has been described in this embodiment was greatly effective.

FIG. 13 is a graph showing measured values (average values, maximum values, and minimum values) shown in Figs. and 12. In the graph of FIG. 13, the horizontal axis indicates the position in the direction of the length of the preform 10, and the vertical axis indicates a width of the through hole 11.

It can be understood, from the graph shown in FIG. 13, that (i) an average size, a maximum size, and a minimum size of the through holes 11, obtained by the inspecting device 100, and (ii) an average size, a maximum size, and a minimum size of the through holes 11, obtained by actual measurement, are substantially equal to each other, that is, almost no error occurs between them.

A is clear from the graph of FIG. 13, the through holes 11 are formed so as to penetrate the preform while sizes of the through holes 11 are set to be substantially constant irrespective of the positions of the through holes 11 in the direction of the length of the preform 10. The inspecting device 100 may be configured to present such graph to a user by, for example, causing (i) a display to display such graph or (ii) a printer to print out the graph, thereby allowing the user to easily grasp positions of the through holes 11 in the preform 10.

Further, the graph of FIG. 13 shows upper and lower limits of the threshold. The upper and lower limits of the threshold are preset to the inspecting device 100. For example, the determining section 112 of the inspecting device 100 can determine whether or not each of the plurality of through holes 11 has an appropriate size depending on whether or not sizes of the plurality of through holes 11 fall within the upper and lower thresholds. The inspecting device 100 may be configured to present such graph to a user by, for example, causing (i) a display to display such graph or (ii) a printer to print out the graph, thereby allowing the user to easily grasp positions of the through holes 11 in the preform 10.

Note that the determining section 112 can determine whether or not each of the plurality of through holes 11 in the preform 10 has an appropriate size depending on whether or not an average size, a maximum size, or a minimum size of the plurality of through holes 11 fall within the upper and lower thresholds.

FIG. 14 and FIG. 15 are cross-sectional views of a preforms 30 and 40, respectively, which are different from the preform 10 of this example in terms of positions of the through holes.

In this example, the inspecting device 100 carried out inspection by use of a preform 10 in which eight (even number of) through holes 11 was formed. However, a preform to be inspected by the inspecting device 100 is not limited to the preform 10. The inspecting device 100 can test various preforms which are different from the preform 10 in the number, a size, a shape, etc. of the through holes 11.

Through holes not subject to the inspection sometimes influence inspection of through holes to be inspected. In response to this, in order to remove influence of the through holes not subject to the inspection, the through holes can be filled with matching oil which has a refractive index equal to a material (e.g., silica glass) of the preform.

The through holes filled with the matching oil have a refractive index which is substantially equal to a periphery of the through holes. This hardly causes reflection or refraction of the light on surfaces of the through holes. For this reason, the inspecting device 100 can accurately inspect the through holes to be inspected as if the through holes not subject to the inspection do not exist.

For example, the preform 30 illustrated in FIG. 14 is formed so that ten through holes are formed in each of two concentric circles having different diameters. In a case where the inspecting device 100 would inspect the through holes of the preform 30 formed on one concentric circle, there is a possibility that the through holes formed on the other concentric circle influence the inspection and the inspecting device 100 cannot obtain an accurate result of the inspection. In order to inspect the through holes formed on the one concentric circle, each of the through holes formed on the other concentric circle may be filled with the matching oil in advance. Accordingly, the inspecting device 100 can accurately inspect the through holes formed on the one concentric circle, without receiving the influence from the through holes formed on the other concentric circle.

Further, in the preform 40 illustrated in FIG. 15, five through holes A through E are formed on the concentric circle. In a case where an interval between, for example, a through hole C and a through hole D of the preform 40 is inspected, the through hole A provided in a position facing those through holes C and D via the center axis of the preform 40 influences a middle position of the bright portion A1, to thereby generate a dark portion. It may be impossible to accurately inspect an interval between the through holes C and D. In order to accurately inspect the interval between the through holes C and D, the through hole A may be filled with the matching oil in advance. For this reason, the inspecting device 100 can appropriately inspect the through holes C and D without receiving the influence of the through hole A. The number of the through holes formed in a preform to be inspected is preferably even number (e.g., six, eight, ten, or twelve). However, since the aforementioned method is employed, it is possible that the inspecting device 100 accurately inspect the through holes of the preform even if the odd number of the through holes is provided in the preform.

A method for filling the matching oil can be manually operated by a tester. In a case where the inspecting device 100 includes filling means, the matching oil can be automatically filled by the filling means. In a case where intensity distributions of inspecting light transmitted from respective directions are detected while the preform is rotated, which through holes are not subject to the inspection would be changed depending on which direction the inspecting light is transmitted from. In this case, the matching oil may be filled and discharged as necessary.

Note that a method for removing the influence of the through holes not subject to the inspection is not limited to this. For example, it is possible to remove the influence (of the through holes not subject to the inspection) by ignoring data of the intensity distributions of the through holes not subject to the inspection.

(Effects)

As described so far, the inspecting device 100 of this embodiment inspects individual intervals between adjacent through holes 11, on the basis of intensity distributions of transmitted light which has been transmitted through a center portion of a preform 10. In addition, sizes of the plurality of through holes 11 are inspected on the basis of the intensity distributions of the transmitted light which has been transmitted through the center portion of the preform 10. That is, the inspecting device 100 of the present invention can inspect the through holes separately, i.e., can inspect (i) positions of the through holes and (ii) a size of the through holes, even though it has been difficult to carry out the inspection by use of a conventional inspecting device (e.g., the inspecting device described in Patent Literature 5).

Specifically, the inspecting device 100 of the present invention is arranged such that an intensity of the inspecting light 20 which irradiates the preform 10 is relatively reduced so that transmitted light transmitted through the center portion of the preform 10 is generated. The inspecting device 100 measures intervals between adjacent through holes 11 on the basis of the width of the bright portion A1 in the intensity distributions of the transmitted light.

Accordingly, the inspecting device 100 of this embodiment can perform nondestructive inspection by which the intervals between adjacent through holes 11 formed in the preform 10 can be accurately determined with relatively lower intensity of the inspecting light 20.

In particular, the inspecting device 100 of this embodiment determines intervals between adjacent through holes 11 on the basis of a maximum width in the time series of the width of the bright portion A1.

Accordingly, the inspecting device 100 of this embodiment can accurately determine intervals between adjacent through holes 11 on the basis of the time series of the width of the bright portion A1, even if positions (and angles) of through holes 11 are not adjusted with the inspecting light 20 and the detector 102. This makes it possible to greatly reduce time and effort for inspecting a preform 10.

Further, the inspecting device 100 of this embodiment is arranged such that a size of each of the through holes 11 is measured on the basis of the width of the dark portion B3 in the intensity distribution of the transmitted light which is transmitted through the center portion of the preform 10.

Accordingly, the inspecting device 100 of this embodiment can perform nondestructive inspection by which a size of each of the through holes 11 formed in the preform can be accurately determined with relatively lower intensity of the inspecting light 20.

In particular, the inspecting device 100 of this embodiment is arranged such that a size of each of the through holes 11 is determined on the basis of a minimum value in the time series of the width of the dark portion B3.

Accordingly, the inspecting device 100 of this embodiment can accurately determine a size of the through holes 11 on the basis of the time series of the width of the dark portion B3, even if positions (and angles) of through holes 11 are not adjusted with the inspecting light 20 and the detector 102. This makes it possible to greatly reduce time and effort for inspecting a preform 10.

Furthermore, the inspecting device 100 of this embodiment can parallel move the preform 10 or the detector 102, by use of the parallel moving mechanism 104, in a direction of the center axis of the preform 10.

This structure allows the inspecting device 100 of this embodiment to perform nondestructive inspection for the preform 10, which nondestructive inspection can accurately determine at least one of a position and size of the through holes 11 individually or as a whole.

Furthermore, the inspecting device 100 of this embodiment is arranged so that the intensity of the inspecting light 20 can be adjusted by the adjusting section 120.

Accordingly, by such a simple structure, i.e., by only adjusting the intensity of the inspecting light 20, the inspecting device 100 of this embodiment can appropriately set a width of transmitted light (which is transmitted through the center portion of the preform 10) in accordance with feature values of (i) the preform 10 and (ii) the through holes 11 formed in the preform 10.

(Supplementary Explanation)

The present invention is not limited to the description of the embodiments above, and can be modified in numerous ways by a skilled person as long as such modification falls within the scope of the claims. An embodiment derived from a proper combination of technical means disclosed in different embodiments is also encompassed in the technical scope of the present invention.

(Summary)

As described above, an inspecting device of this embodiment includes: detecting means for sequentially detecting an intensity distribution of transmitted light which (i) has entered a side surface of a columnar preform having through holes and (ii) has been transmitted through a center portion of the preform; rotating/moving means for (a) moving the preform so that the preform is rotated about a center axis of the preform, the center axis serving as a rotating axis, or (b) moving the detecting means so that the detecting means rotates around the preform; and calculating means for calculating a time series of a feature value from the intensity distribution of the transmitted light, which intensity distribution has been sequentially detected, the feature value having a value corresponding to at least one of (i) arrangement of the through holes and (ii) a size of each of the through holes.

In a case of forward scattered light, its intensity distribution has a dark portion corresponding to a shadow of a region which includes all the through holes. On the contrary, in a case of transmitted light, its intensity distribution has a dark portion corresponding to a shadow of one through hole. Conventionally, it has been difficult to specify (i) arrangement of the through holes or (ii) a size of the through holes on the basis of the time series of the feature value calculated from the intensity distribution of the forward scattered light. However, according to the arrangement, it is possible to precisely specify the through holes separately, i.e., to precisely specify the arrangement and the size. Furthermore, according to the arrangement, the inspecting device does not detect the intensity distribution of the forward scattered light, but detects the intensity distribution of the transmitted light, so that it is unnecessary to cause high-intensity parallel light to enter the preform, unlike a case of detecting the intensity distribution of the forward scattered light.

That is, according to the arrangement, it is possible to precisely inspect whether or not each of the through holes is formed in an appropriate position with an appropriate size, without (i) using high-intensity parallel light and (ii) destroying the preform.

It is preferable that, in the inspecting device in accordance with the present invention, the feature value is a width of a bright portion formed in a center of the intensity distribution.

The intensity distribution of the transmitted light has a bright portion in its center, and the bright portion has a width corresponding to an interval between two through holes adjacent to each other among all the through holes formed in the preform.

According to the arrangement, it is possible to precisely inspect whether or not the through holes are formed at appropriate intervals.

It is preferable that the inspecting device in accordance with the present invention further includes determining means for determining whether or not the through holes are formed at an appropriate interval by comparing, with a preset threshold value, a maximum value in the time series of the width of the bright portion.

According to the arrangement, it is possible to automatically determine whether or not the through holes are formed at appropriate intervals. This makes it possible to largely reduce time and effort relating to the inspection.

It is preferable that, in the inspecting device in accordance with the present invention, the feature value is a width of a dark portion which is formed between two bright portions formed in a vicinity of a center of the intensity distribution.

The intensity distribution of the transmitting light has two bright portions in the vicinity of the center of the intensity distribution, and a dark portion between the two bright portions has a width corresponding to a size (diameter) of a through hole formed in the preform. According to the arrangement, it is possible to precisely inspect whether or not each of the through holes is formed with an appropriate size.

It is preferable that the inspecting device in accordance with the present invention further includes determining means for determining whether or not each of the through holes is formed with an appropriate size by comparing, with a preset threshold value, a minimum value in the time series of the width of the dark portion.

According to the arrangement, it is possible to automatically determine whether or not each of the through holes is formed with an appropriate size. This makes it possible to largely reduce time and effort relating to the inspection.

It is preferable that the inspecting device in accordance with the present invention, the detecting means sequentially detects not only the intensity distribution of the transmitted light which has been transmitted through the center portion of the preform but also an intensity distribution of passing light which has traveled outside the preform;

a bright portion corresponding to the transmitted light, which is formed in a center of the intensity distribution, represents a first bright portion, and bright portions corresponding to the passing light, which are formed in both ends of the intensity distribution, represent a second bright portion and a third bright portion, respectively; and a ratio of a first interval to a second interval is used as a feature value, where the first interval is an interval between the first bright portion and the second bright portion, and the second interval is an interval between the first bright portion and the third bright portion.

The first interval between the first bright portion and the second bright portion corresponds to an interval between a through hole and the most external portion of the preform. Further, the second internal between the first bright portion and the third bright portion corresponds to an interval between the through hole and the other most external portion of the preform. According to the arrangement, it is possible to precisely inspect the position of the through hole with respect to the center axis on the basis of a ratio of the first interval to the second interval, without performing time-consuming and troublesome processes (such as adjusting the position of the center axis, detecting of the position of the center axis, and measuring of a distance between the center axis and the through holes).

It is preferable that the inspecting device in accordance with the present invention further includes determining means for determining whether or not each of the through holes is formed in an appropriate position with respect to the center axis by comparing, with a preset threshold value, the ratio of the first interval to the second interval.

According to the arrangement, it is possible to automatically determine whether or not the through holes are formed in respective appropriate positions with respect to the center axis. This makes it possible to largely reduce time and effort relating to the inspection.

It is preferable that the inspecting device in accordance with the present invention further includes parallel moving means for parallel moving the preform or the detecting means in a direction of the center axis of the preform.

According to this arrangement, it is possible to nondestructive perform inspection to accurately specify at least one of (i) arrangement of the through holes and (i) a size of each of the through holes in a cross-section of the preform.

It is preferable that the inspecting device in accordance with the present invention further includes adjusting means for adjusting intensity of inspecting light which will enter the preform.

According to the arrangement, a range in which the inspecting light is transmitted through the preform can be determined so as to be an appropriate range in accordance with features (e.g., a curvature of a surface of the preform and a material of the preform) of the preform and features (e.g., positions and widths of through holes, and an interval between through holes) of the through holes formed in the preform.

In order to attain the above-mentioned object, an inspecting method in accordance with the present invention includes the steps of: (A) sequentially detecting, by use of detecting means, an intensity distribution of transmitted light which (i) has entered a side surface of a columnar preform having through holes and (ii) has been transmitted through a center portion of the preform; (B) (a) moving the preform so that the preform is rotated about a center axis of the preform, the center axis serving as a rotating axis, or (b) moving the detecting means so that the detecting means rotates around the preform; (C) calculating a time series of a feature value from the intensity distribution of the transmitted light, which intensity distribution has been sequentially detected, the feature value having a value corresponding to at least one of (i) arrangement of the through holes and (ii) a size of each of the through holes; and (D) determining whether or not the at least one of (i) the arrangement of the through holes and (ii) the size of each of the through holes is appropriate on the basis of the time series of the feature value calculated in the step of (C).

According to the present invention, the inspecting method has an effect which is similar to that of the inspecting device of the present invention.

It is possible that the inspecting method in accordance with the present invention further includes the steps of, before any of the steps, filling matching oil into a through hole not subject to the inspection.

According to this arrangement, it is possible to (i) remove an influence of the through holes not subject to the inspection and (ii) accurately inspect the through holes to be inspected by filling a matching oil to the through holes not subject to the inspection.

Further, a method for manufacturing an optical fiber in accordance with the present invention includes one of inspecting methods.

According to the present invention, the method for manufacturing an optical fiber has an effect which is similar to that of the inspecting method of the present invention.

Industrial Applicability

An inspecting method of the present invention can be used to inspect various kinds of preform, provided that the preform is a base material for an optical fiber (holey fiber) in which holes are formed, such as a hole assisted fiber and a photonic bandgap fiber.

Reference Signs List 10 preform
11 through hole
20 inspecting light
101 light source
102 detector (detecting means)
103 rotating mechanism (rotating/moving means)
104 parallel moving mechanism (parallel moving means)
110 control circuit
111 calculating section (calculating means)
112 determining section (determining means)
114 position detecting section
116 recording section
118 display control section
120 adjusting section (adjusting means)

The invention claimed is:

1. An inspecting device, comprising:
    detecting means for sequentially detecting an intensity distribution of transmitted light which (i) has entered a side surface of a columnar preform having through holes and (ii) has been transmitted through a center portion of the preform;
    moving means for (a) moving the preform so that the preform is rotated about a center axis of the preform, the center axis serving as a rotating axis, or (b) moving the detecting means so that the detecting means rotates around the preform; and
    calculating means for calculating a time series of a feature value from the intensity distribution of the transmitted light, which intensity distribution has been sequentially detected, the feature value having a value corresponding to at least one of (i) arrangement of the through holes and (ii) a size of each of the through holes.

2. The inspecting device as set forth in claim 1, wherein the feature value is a width of a bright portion formed in a center of the intensity distribution.

3. The inspecting device as set forth in claim 2, further comprising:
    determining means for determining whether or not the through holes are formed at an appropriate interval by comparing, with a preset threshold value, a maximum value in the time series of the width of the bright portion.

4. The inspecting device as set forth in claim 1, wherein the feature value is a width of a dark portion which is formed between two bright portions formed in a vicinity of a center of the intensity distribution.

5. The inspecting device as set forth in claim 4, further comprising
    determining means for determining whether or not each of the through holes is formed with an appropriate size by comparing, with a preset threshold value, a minimum value in the time series of the width of the dark portion.

6. The inspecting device as set forth in claim 1, wherein: the detecting means sequentially detects not only the intensity distribution of the transmitted light which has been transmitted through the center portion of the preform but also an intensity distribution of passing light which has traveled outside the preform;
    a bright portion corresponding to the transmitted light, which is formed in a center of the intensity distribution, represents a first bright portion, and bright portions corresponding to the passing light, which are formed in both ends of the intensity distribution, represent a second bright portion and a third bright portion, respectively; and
    a ratio of a first interval to a second interval is used as a feature value, where the first interval is an interval between the first bright portion and the second bright portion, and the second interval is an interval between the first bright portion and the third bright portion.

7. The inspecting device as set forth in claim 6, further comprising
    determining means for determining whether or not each of the through holes is formed in an appropriate position with respect to the center axis by comparing, with a preset threshold value, the ratio of the first interval to the second interval.

8. The inspecting device as set forth in claim 1, further comprising
    parallel moving means for parallel moving the perform or the detecting means in a direction of the center axis of the preform.

9. The inspecting device as set forth in claim 1, further comprising
    adjusting means for adjusting intensity of inspecting light which will enter the preform.

10. An inspecting method, comprising the steps of:
    (A) sequentially detecting, by use of detecting means, an intensity distribution of transmitted light which (i) has entered a side surface of a columnar preform having through holes and (ii) has been transmitted through a center portion of the preform;
    (B) (a) moving the preform so that the preform is rotated about a center axis of the preform, the center axis serving as a rotating axis, or (b) moving the detecting means so that the detecting means rotates around the preform;
    (C) calculating a time series of a feature value from the intensity distribution of the transmitted light, which intensity distribution has been sequentially detected, the feature value having a value corresponding to at least one of (i) arrangement of the through holes and (ii) a size of each of the through holes; and
    (D) determining whether or not the at least one of (i) the arrangement of the through holes and (ii) the size of each of the through holes is appropriate on the basis of the time series of the feature value calculated in the step of (C).

11. The inspecting method as set forth in claim 10, further comprising the steps of before any of the steps, filling matching oil into a through hole not subject to the inspection.

12. A method for manufacturing an optical fiber, comprising the steps of:
   (A) sequentially detecting, by use of detecting means, an intensity distribution of transmitted light which (i) has entered a side surface of a columnar preform having through holes and (ii) has been transmitted through a center portion of the preform;
   (B) (a) moving the preform so that the preform is rotated about a center axis of the preform, the center axis serving as a rotating axis, or (b) moving the detecting means so that the detecting means rotates around the preform;
   (C) calculating a time series of a feature value from the intensity distribution of the transmitted light, which intensity distribution has been sequentially detected, the feature value having a value corresponding to at least one of (i) arrangement of the through holes and (ii) a size of each of the through holes; and
   (D) determining whether or not the at least one of (i) the arrangement of the through holes and (ii) the size of each of the through holes is appropriate on the basis of the time series of the feature value calculated in the step of (C).

* * * * *